United States Patent
Hayashi et al.

(10) Patent No.: US 8,652,521 B2
(45) Date of Patent: *Feb. 18, 2014

(54) COATED SOLID PREPARATION

(75) Inventors: Yuki Hayashi, Kamakura (JP); Ryoji Yoshii, Kamakura (JP); Yasuhide Horiuchi, Kamakura (JP)

(73) Assignee: Toray Industries, Inc. (JP)

( * ) Notice: Subject to any disclaimer, the term of this patent is extended or adjusted under 35 U.S.C. 154(b) by 152 days.

This patent is subject to a terminal disclaimer.

(21) Appl. No.: 13/201,546

(22) PCT Filed: Mar. 3, 2010

(86) PCT No.: PCT/JP2010/053383
§ 371 (c)(1),
(2), (4) Date: Aug. 15, 2011

(87) PCT Pub. No.: WO2010/110018
PCT Pub. Date: Sep. 30, 2010

(65) Prior Publication Data
US 2011/0305756 A1    Dec. 15, 2011

(30) Foreign Application Priority Data
Mar. 27, 2009  (JP) ................. 2009-078976

(51) Int. Cl.
*A61K 31/19*  (2006.01)
*A61K 9/32*   (2006.01)

(52) U.S. Cl.
USPC ................. 424/482; 424/474; 514/557

(58) Field of Classification Search
None
See application file for complete search history.

(56) References Cited

U.S. PATENT DOCUMENTS

| | | | |
|---|---|---|---|
| 6,197,348 B1 | 3/2001 | Morella et al. | |
| 6,495,163 B1 * | 12/2002 | Jordan | 424/474 |
| 2004/0208927 A1 * | 10/2004 | Safadi et al. | 424/465 |
| 2004/0241287 A1 * | 12/2004 | Bastiaans et al. | 426/89 |

FOREIGN PATENT DOCUMENTS

| | | | |
|---|---|---|---|
| EP | 1985585 | * 10/2008 | C01B 33/44 |
| JP | 2000-509399 A | 7/2000 | |
| JP | 2006-83162 A | 3/2006 | |
| JP | 2006-160627 A | 6/2006 | |
| JP | 2006-256961 A | 9/2006 | |
| WO | WO 02/586666 A2 | 8/2002 | |
| WO | 2004-521890 A | 7/2004 | |

OTHER PUBLICATIONS

"Iyakuhin Tenkabutsu Jiten 2007," Yakuji Nippo Ltd., Jul. 25, 2007, p. 251, (Partial English translation by inventors.).

* cited by examiner

*Primary Examiner* — Rachael E Bredefeld
(74) *Attorney, Agent, or Firm* — DLA Piper LLP (US)

(57) ABSTRACT

A coated solid preparation includes an active ingredient including valproic acid or a pharmacologically acceptable salt thereof, and a coating layer containing polyvinyl alcohol and swelling clay coating the active ingredient wherein mass ratio of the polyvinyl alcohol to the swelling clay is 8:2 to 3:7 and the swelling clay is dispersed as a laminated structure.

4 Claims, 1 Drawing Sheet

COATED SOLID PREPARATION

RELATED APPLICATIONS

This is a §371 of International Application No. PCT/JP2010/053383, with an international filing date of Mar. 3, 2010 (WO 2010/110018 A1, published Sep. 30, 2010), which is based on Japanese Patent Application No. 2009-078976, filed Mar. 27, 2009, the subject matter of which is incorporated by reference.

TECHNICAL FIELD

This disclosure relates to a coated solid preparation.

BACKGROUND

Valproic acid, which is useful as an antiepileptic drug, has been widely administered to treat epilepsy and prevent seizures. However, valproic acid deliquesces only by being left to stand at room temperature because of its high hygroscopicity. Therefore, there is no valproic acid preparation that is applicable to a one-dose pack. Thus, there is a need for development of a preparation that has stability against moisture and does not deliquesce under normal storage conditions.

Known methods for improving the deliquescence of valproic acid include, for example, a method of blending a solid preparation with a non-hygroscopic excipient (JP 2004-521890A), a method of sugar-coating (JP 2006-256961A), a method of film-coating with macromolecular substances (JP 2006-83162A), and a method of packaging with packaging materials having high water vapor barrier properties.

For example, JP 2004-521890A discloses a method of mixing sodium valproate, carbomer, and a non-hygroscopic additive to a homogeneous state and compressing the resulting mixture into tablets, which tablets have properties of absorbing up to 5% by weight of water even when stored at 75% relative humidity for three months.

JP 2006-256961A discloses tablets produced by sugar-coating sodium valproate sequentially with a first layer composed of sucrose soluble in water and organic solvents, a second layer composed of macromolecules and sucrose soluble in water and organic solvents, a third layer composed of sucrose, and a fourth layer composed of macromolecules, sucrose, and the like, which tablets have stability against moisture.

JP 2006-83162A discloses double-coated tablets in which a first coating layer is formed from a coating agent mainly composed of starch and sugar, and a second coating layer is formed thereon from a coating agent mainly composed of macromolecules, which double-coated tablets suppresses the deliquescence of the deliquescent drug contained as an active ingredient.

As a method of packaging with packaging materials having high water vapor barrier properties, the method of protecting a solid preparation from moisture by placing the solid preparation in a PTP (press through pack) sheet laminated with polyvinylidene chloride and sealing the sheet is used in various medicaments.

On the other hand, to prevent patients from forgetting to take prescribed drugs or taking a wrong dose, one-dose packs are now in widespread use at clinical sites and dispensing pharmacies. Taking a plurality of solid preparations to be taken in one dose out of packaging materials such as a PTP sheet and putting them in one package to provide to patients have become predominant.

However, in one-dose packing, each solid preparation will be stored for a long period of time in an automatic packaging machine in a naked state as taken out of a PTP sheet in advance. Therefore, for preparations which have low stability against moisture and contain as an active ingredient valproic acid having deliquescence, it is difficult at present to use a one-dose pack. That is, patients who receive a preparation containing valproic acid as an active ingredient have not gained the advantage of one-dose packs that they improve drug compliance to enhance the therapeutic effect. There is a need for improvement in this regard.

There are methods, as disclosed in JP 2004-521890A, JP 2006-256961A and JP 2006-83162A, for improving the stability against moisture of a preparation containing sodium valproate. However, in these methods, increase in size of a solid preparation due to coating cannot be avoided, making it difficult for patients to ingest. Hence, it is difficult at present to put the preparation into practice. In particular, the method of sugar-coating a solid preparation, as disclosed in JP 2006-256961A, not only requires a long period of time for the process of sugar-coating, but also has a problem in that, under high humidity, it exhibits poor moisture barrier properties and cannot suppress deliquescence and liquefaction. Further, the double-coated tablet disclosed in JP 2006-83162A requires strict control of the production conditions because it requires multiple coating steps, so that, in view of both production time and production cost, it is difficult to apply it to a preparation containing sodium valproate.

Thus, it could be helpful to provide a coated solid preparation applicable to a one-dose pack, wherein, even when the preparation is in an unpacked state, the stability against moisture of valproic acid or a pharmacologically acceptable salt thereof contained therein is maintained and the deliquescence is suppressed.

SUMMARY

We provide a coated solid preparation including an active ingredient including valproic acid or a pharmacologically acceptable salt thereof and a coating layer containing polyvinyl alcohol and swelling clay coating the active ingredient wherein mass ratio of the polyvinyl alcohol to the swelling clay is 8:2 to 3:7 and the swelling clay is dispersed as a laminated structure.

We also provide the above-mentioned coated solid preparation wherein the swelling clay is bentonite or magnesium aluminum silicate.

We further provide the above-mentioned coated solid preparation wherein water vapor permeability of the coating layer is $1.0 \times 10^{-5}$ to $1.0 \times $g·mm/cm$^2$·24 hr·atm.

DETAILED DESCRIPTION

Figure 1:
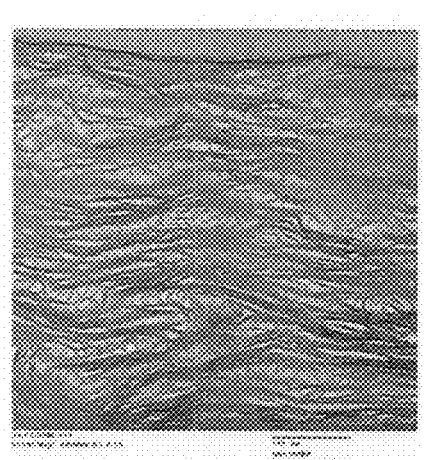
FIG. 1 is a focused ion beam transmission electron microscopy image of the film of Example 1.

We discovered that a coated solid preparation with significantly improved stability, against moisture can be obtained by coating a solid preparation containing as an active ingredient valproic acid or a pharmacologically acceptable salt thereof with a coating agent containing a particular component in a particular state without increasing the size of the coated solid preparation (without posing any problem in patients' taking the coated solid preparation).

Thus, we provide a coated solid preparation comprising as an active ingredient valproic acid or a pharmacologically acceptable salt thereof; the preparation being coated with a coating layer containing polyvinyl alcohol and swelling clay; the mass ratio of the polyvinyl alcohol to the swelling clay being 8:2 to 3:7; and the swelling clay being dispersed as a laminated structure.

The above coating layer does not pose any problem in patients' taking the coated solid preparation because it is a thin film layer, and the swelling clay can improve the stability against moisture of the coated solid preparation and also effectively prevent deliquescence of valproic acid or a pharmacologically acceptable salt thereof because it fully exerts a path effect by being dispersed as a laminated structure in a swollen state.

The swelling clay is preferably bentonite or magnesium aluminum silicate, and water vapor permeability of the above coating layer is still more preferably $1.0 \times 10^{-5}$ to $1.0 \times 10^{-4}$ g·mm/cm$^2$·24 hr·atm.

Bentonite and magnesium aluminum silicate have very large aspect ratio. Therefore, they can produce a larger path effect in a coating layer formed on the surface of a solid preparation and further improve stability against moisture of the coated solid preparation.

We provide a coated solid preparation applicable to a one-dose pack, wherein, even when the preparation is in an unpacked state, stability against moisture of valproic acid or a pharmacologically acceptable salt thereof contained therein is maintained and deliquescence is suppressed. The coating layer in the coated solid preparation does not pose any problem in patients' taking the coated solid preparation because it is a thin film layer, and the swelling clay can improve stability against moisture of the coated solid preparation and also effectively prevent deliquescence of valproic acid or a pharmacologically acceptable salt thereof because it fully exerts a path effect by being dispersed as a laminated structure in a swollen state. Furthermore, the coated solid preparation can be used not only as a sustained-release preparation, but also as an immediate-release preparation because it has excellent disintegration properties as well as excellent stability against moisture.

Preferred examples of our preparations will now be described. It should be understood, however, that this disclosure is not limited to the following examples, and unless otherwise specified, "%" means "mass/mass percentage (w/w %)".

The coated solid preparation is characterized in that it contains as an active ingredient valproic acid or a pharmacologically acceptable salt thereof and is coated with a coating layer containing polyvinyl alcohol and swelling clay, wherein the mass ratio of the polyvinyl alcohol to the swelling clay is 8:2 to 3:7 and the swelling clay is dispersed as a laminated structure.

"Solid preparation" refers to a pharmaceutical formulated to be a solid, examples of which include tablets (including sublingual tablets and orally disintegrating tablets), capsules (including soft capsules and microcapsules), granules, fine granules, powders, pills, troches, and films. "Coated solid preparation" refers to a preparation in which a coating layer is formed to prevent the pharmacologically active components from, for example, being decomposed by oxygen, water vapor, light, and the like by coating the surface of the above solid preparation with a coating agent.

Examples of "valproic acid or pharmacologically acceptable salt thereof" include valproic acid, sodium valproate, semisodium valproate, sodium hydrogen divalproate, divalproex, magnesium valproate, zinc valproate, potassium valproate, and lithium valproate. Examples of commercially available preparations of sodium valproate include Selenica tablet (Kowa Company, Ltd.), Selenica R tablet (Kowa Company, Ltd.), Selenica R granule (Kowa Company, Ltd.), Valerin tablet (Dainippon Sumitomo Pharma Co., Ltd.), Hyserenin tablet (Schering-Plough Corporation), Depakene tablet (Kyowa Hakko co., ltd.), Depakene R tablet (Kyowa Hakko co., ltd.), and Depakene fine granule (Kyowa Hakko co., ltd.). Examples of commercially available preparations of divalproex include Depakote tablet (Abbott).

"Polyvinyl alcohol" refers to an alcohol obtained by saponifying polyvinyl acetate, including from partially saponificated polyvinyl alcohols having several ten percent of residual acetic acid groups to completely saponificated polyvinyl alcohols having only a few percent of residual acetic acid groups. The saponification degree of polyvinyl alcohol is preferably 70 to 97 mol %, and the average degree of polymerization is preferably 200 to 3000, more preferably 600 to 2400.

The above polyvinyl alcohol may be used by mixing two or more polyvinyl alcohols having different saponification degrees and average degrees of polymerization. When mixing two or more polyvinyl alcohols, for example, a polyvinyl alcohol of low polymerization degree grade may be added and then a polyvinyl alcohol of high polymerization degree grade may be mixed therewith. Examples of polyvinyl alcohols include various types of Poval (Kuraray Co., Ltd.) and Gohsenol (Nippon Synthetic Chemical Industry Co., Ltd.).

"Swelling clay" refers to clay having swelling properties, more particularly to a finely-powdered substance which, when soaked with an appropriate amount of water, exhibits viscosity and plasticity and also has swelling properties. Swelling clay is preferably one which is negatively charged due to the compositional balance of metal salt species, examples of which include smectites such as hydrated aluminum silicate having a three-layer structure. Negatively charged means the state in which the swelling clay has a cation-exchange capability, and the amount of charge is expressed as Cation Exchange Capacity (CEC). The unit, of cation exchange capacity is milliequivalent/100 gram (usually expressed as meq/100 g), and generally expressed as the number of equivalent corresponding to the molar concentration of monovalent ions. Preferred examples of the swelling clay contained in the above coating layer include hydrated aluminum silicate having a three-layer structure, for example, smectites. Examples of smectites include beidellite, nontronite, saponite, hectorite, sauconite, bentonite, and magnesium aluminum silicate. These may be used alone or two or more of these may be used in combination if desired. Among these smectites, preferred are bentonite and magnesium aluminum silicate, and more preferred is bentonite. For the above swelling clay, as long as stability against moisture of valproic acid or a pharmacologically acceptable salt thereof is not decreased, these may be used in combination.

"Swelling clay in a swollen state" refers to the swelling clay which has been swollen by soaking the above swelling clay with water. Preferred swelling clay in a swollen state is, for example, the swelling clay such that a dispersion obtained by suspending swelling clay in a dispersion medium such as water and stirring the suspension with a homogenizer or the like is dispersed to the extent that the dispersion can be completely filtered through a filter paper. As a filter paper used, for example, No. 5B quantitative filter paper (ADVANTEC) is more preferable.

The above swelling clay is dispersed preferably as a laminated structure. "Laminated structure" refers to the laminated structure formed by stacking of a plurality of layered structures, particularly to the laminated structure in which 10 to 100 layers of the band of swelling clay are stacked. The surface of the solid preparation may be coated with the coating agent in which the swelling clay is dispersed in a swollen state for the above swelling clay to form a laminated structure.

"Coating layer" means a layer of a film formed by coating a solid preparation with a coating agent, the layer being for the purpose of preventing the pharmacologically active components contained in the solid preparation from, for example, being decomposed by oxygen, water vapor, light, and the like. The coating layer contains the above polyvinyl alcohol and swelling clay, and the mass ratio of polyvinyl alcohol to swelling clay is preferably 8:2 to 3:7, more preferably 4:6 to 6:4. This is because when the mass of swelling clay is less than one fourth of the mass of polyvinyl alcohol, the path effect of the swelling clay is reduced, so that the stability against moisture of valproic acid or a pharmacologically acceptable salt thereof cannot be sufficiently obtained, and when the mass of swelling clay is above 2.3 times the mass of polyvinyl alcohol, the layer structure of the coating layer becomes non-uniform because of the too high ratio of swelling clay, so that the sufficient barrier properties cannot be obtained. The percentage of swelling clay in the above coating layer is preferably 5% or more based on the total coating layer.

The water vapor permeability of the above coating layer is preferably $1.0 \times 10^{-5}$ to $1.0 \times 10^{-4}$ g·mm/cm$^2$·24 hr·atm, more preferably $1.0 \times 10^{-5}$ to $6.0 \times 10^{-5}$ g·mm/cm$^2$·24 hr·atm, especially preferably $1.0 \times 10^{-5}$ to $3.5 \times 10^{-5}$ g·mm/cm$^2$·24 hr·atm.

Measurement of water vapor permeability may be made, for example, in accordance with the standard specification in the art, JIS K8123 (1994. This method, if desired, may be partially modified to make the measurement, as described in the Examples herein.

The coating agent used to form the above coating layer, which agent contains the above polyvinyl alcohol and swelling clay, is prepared by dispersing the polyvinyl alcohol and swelling clay in a suitable solvent, depending on the intended use, and can coat the solid preparation containing valproic acid or a pharmacologically acceptable salt thereof which is a pharmacologically active component.

Examples of the solvents used to prepare the coating agent include water, organic solvents, and mixed water-organic solvent system, among which water is especially preferred. Examples of the organic solvents include C1-C5 lower alcohols or mixed solvents thereof.

The above coating layer is preferably coated, by coating with the above coating agent, over 2 to 200% of the solid preparation, and when the solid preparation is in the form of a tablet, the coverage is preferably 3 to 30%, more preferably 3 to 20%, still more preferably 3 to 10%.

Examples of the method of coating the solid preparation with the coating agents include, for example, in the case where the inner layer is in the form of a tablet, the method using coating pans, coating machines for tablets, or the like, and in the case where the inner layer is in the form of granules or powders, the method using fluidized-bed coating machines, rolling fluidized-bed coating machine, or the like.

Additives commonly used by those skilled in the art may be further added to the above coating layer and coating agent. Examples of such additives include coloring agents such as dyes extracted from plants and masking agents such as titanium oxide, calcium carbonate, and silicon dioxide.

As long as the stability against moisture of valproic acid or a pharmacologically acceptable salt thereof is not decreased, pharmaceutically acceptable additives may be added to the above coated solid preparation. For example, surfactants may be added to improve dispersibility of swelling clay.

To impart disintegration properties to the coated solid preparation, for example, saccharides and sugar alcohols such as maltose, maltitol, sorbitol, xylitol, fructose, glucose, lactitol, isomaltose, lactose, erythritol, mannitol, trehalose, or sucrose, and disintegrants such as croscarmellose sodium and low substituted hydroxypropylcellulose may be added to the above coating layer or the coating agent used for coating. To increase the robustness of the coated solid preparation, plasticizers such as triethyl citrate, polyethylene glycol, and glycerin may be added to the above coating layer or the coating agent used for coating.

However, care should be taken when determining the amount of the above additives commonly used by those skilled in the art, the above pharmaceutically acceptable additives, and the above disintegrants and plasticizers. As described above, an important point is that the coating layer is one in which laminated structures in which 10 to 100 layers of the band of swelling clay are stacked are formed, the band referring to the state in which the swelling clays have consecutive and continuous contacting surfaces each other. If the above additives or the like are excessively or non-uniformly added, discontinuous parts where swelling clays are not in contact each other may be present, and the presence of the discontinuous parts can impair the moisture barrier properties of the coating layer.

The presence of discontinuous parts due to excessive addition of the above additives can be confirmed using the focused ion beam technique by observing the longitudinal section of a coating layer with a transmission electron microscope. That is, when discontinuous parts of the swelling clay are observed in the thickness direction of the coating layer, the moisture barrier properties of the coating layer can be impaired.

The above coated solid preparation may be one which has, further outside the above coating layer, other functional films composed of, for example, gastric-soluble or enteric-soluble macromolecular substances, and also may be one which has, inside the above coating layer, other functional films composed of, for example, gastric-soluble or enteric-soluble macromolecular substances.

EXAMPLES

Our preparations will now be described in detail by way of examples, but this disclosure is not limited to the examples below.

(Method of Measuring Water Vapor Permeability)

The measurement of water vapor permeability was made in accordance with the standard specification in the art, JIS K8123 (1994), with minor modifications. First, the film prepared by the method described below was cut, with light passing therethrough, at a portion of uniform thickness without a pinhole into a circle 3.5 cm in diameter, and the thickness of the film was measured at any five points.

Next, 3 g of calcium chloride (particle size: 850 to 2000 μm) was placed in an aluminum cup (diameter: 30 mm), and the film cut into a circle and a ring for fixing the film were sequentially placed on the aluminum cup. The ring was fixed by placing a weight on the ring, and in this state, molten paraffin wax was poured into the edge of the aluminum cup. After the paraffin wax was solidified, the weight was removed, and the mass of the whole aluminum cup was measured, which was defined as the initial mass. Then, the aluminum cup was placed in a thermostat bath at 40° C. and 75% RH. The aluminum cup was taken out every 24 hours for measuring the mass to calculate the water vapor permeability coefficient by using the following equation. In all the water vapor permeability measurements described below, r=1.5 cm, t=24 hours, and C=1 atm.

Water vapor permeability P (g·mm/cm$^2$·24 hr·atm)=W·A/B·t·C

W: Mass increased in 24 hours (g)
A: Mean value of film thickness at five points (mm)
B: Permeability area $\pi r^2$ (cm$^2$)
t: Elapsed time (hr)
C: Atmosphere (atm)

Example 1

To 177.5 parts by mass of water were added 10.0 parts by mass of polyvinyl alcohol (EG-05; Nippon Synthetic Chemical Industry Co., Ltd.) and 312.5 parts by mass of bentonite solution, and the resulting mixture was stirred with a homogenizer (Polytron Model KR) to obtain a coating agent. The 3.2% bentonite solution used was obtained by adding 32 parts by mass of bentonite (Kunipia-F; KUNIMINE INDUSTRIES CO., LTD., cation exchange capacity: 115 meq/100 g) to 968 parts by mass of stirred water, dispersing the resulting mixture homogeneously with the homogenizer, and suction-filtering the resultant through a filter paper. Hereinafter, polyvinyl alcohol and bentonite may also be referred to as PVA and BT, respectively, for short.

To the coating pan (DRC-200; Powrex Corp.), 200 g of sodium valproate sustained-release tablets (Selenica R 200 mg; Kowa Company, Ltd.) were loaded, and the tablets were coated with the coating agent prepared in Example 1 to a thickness of 20 μm. For the coated solid preparation obtained, the appearance change of the tablets over time when left to stand under the conditions of 25° C. and 60% RH was observed.

Portions of the coating agent obtained in Example 1 were taken, sprayed onto the back of a polypropylene balance tray, and immediately dried with hot air from a dryer. Spraying and drying with a dryer were repeated several times, and then the balance tray was left to stand in an oven at 50° C. and dried overnight. A film was obtained and the water vapor permeability was measured.

Examples 2 and 3

Water, PVA, and BT solution were mixed to give the compositions shown in Table 1. Coated solid preparations were obtained by the method of Example 1, and the appearance change of tablets over time was observed. Films were also obtained by the method of Example 1, and the water vapor permeability was measured.

Examples 4 and 5

Water, PVA, and BT solution were mixed to give the compositions shown in Table 1. Films were obtained by the method of Example 1, and water vapor permeability was measured.

Comparative Example 1

The appearance change of the tablets over time when sodium valproate sustained-release tablets (Selenica R 200 mg; Kowa Company, Ltd.) were left to stand under the conditions of 25° C. and 60% RH was observed.

Comparative Examples 2 to 4

Water, PVA, and BT solution were mixed to give the compositions shown in Table 1. Coated solid preparations were obtained by the method of Example 1, and the appearance change of tablets over time was observed. Films were also obtained by the method of Example 1, and the water vapor permeability was measured.

Table 1 shows deliquescence (appearance change over time) of the tablets and water vapor permeability of the films obtained in Examples 1 to 3 and Comparative Examples 1 to 4 and water vapor permeability of the films obtained in Examples 4 and 5. In the table, the symbol "o" means no change, and "x" means that the exudation of deliquesced drugs out of the tablets was observed.

TABLE 1

|  | PVA/BT | Deliquescence 2-week storage | Deliquescence 4-week storage | Water vapor permeability of the film (g·mm/cm$^2$·24 hr·atm) |
|---|---|---|---|---|
| Comparative Example 1 | — | x | x | — |
| Comparative Example 2 | 1/9 | x | x | 6.2 × 10$^{-4}$ |
| Comparative Example 3 | 2/8 | x | x | 1.4 × 10$^{-4}$ |
| Comparative Example 4 | 9/1 | x | x | 2.3 × 10$^{-4}$ |
| Example 1 | 5/5 | o | o | 2.5 × 10$^{-5}$ |
| Example 2 | 8/2 | o | o | 5.8 × 10$^{-5}$ |
| Example 3 | 3/7 | o | o | 5.2 × 10$^{-5}$ |
| Example 4 | 4/6 | — | — | 3.4 × 10$^{-5}$ |
| Example 5 | 6/4 | — | — | 3.2 × 10$^{-5}$ |

As can be seen from Table 1, it was proved that, when the mass ratio of PVA to BT (PVA/BT) is 8:2 to 3:7, deliquescence of sodium valproate can be suppressed to obtain stable solid preparations. It also became clear from evaluation of water vapor permeability that the solid preparations coated with a film having water vapor permeability of 1.0×10$^{-4}$ or less are very stable against moisture.

(Measurement of Film by Transmission Electron Microscope)

Using the focused ion beam technique, the longitudinal section of the films of Example 1 and Comparative Example 4 was observed under a transmission electron microscope. The micrograph of Example 1 is shown in FIG. 1, and the micrograph of Comparative Example 4 is shown in FIG. 2.

Figure 2:
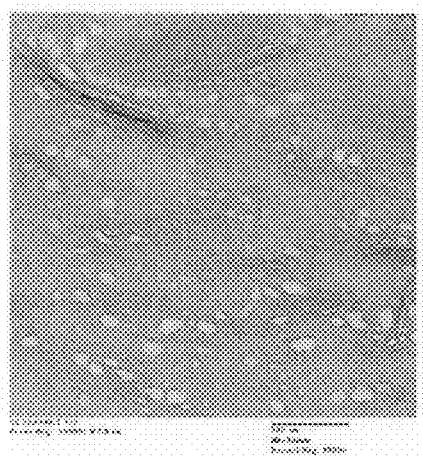
FIG. 2 is a focused ion beam transmission electron microscopy image of the film of Comparative Example 2.

In FIG. 1, it was observed that BT, as a laminated structure, had consecutive and continuous contacting surfaces each other and was homogeneously dispersed in the film. In FIG. 2, on the other hand, BT formed few laminated structures and the discontinuous parts of BT were observed in the thickness direction (the upper and lower direction in FIG. 2) of the film, suggesting that the homogeneous dispersion of the laminated structures of BT significantly contributes to reduced water vapor permeability and the stability against moisture of solid preparations.

Example 6

To 17.32 parts by mass of water and 390.0 parts by mass of ethanol were added 5.28 parts by mass of PVA, 385.0 parts by mass of BT solution, and 2.4 parts by mass of sorbitan monolaurate, and the resulting mixture was stirred with a homogenizer to obtain a coating agent. A film was obtained by the method of Example 1, and water vapor permeability was measured. Hereinafter, sorbitan monolaurate may be referred to as Span 20 for short.

Comparative Example 5

To 480.0 parts by mass of water were added 16.0 parts by mass of PVA and 4.0 parts by mass of BT, and the resulting mixture was stirred with a magnetic stirrer for 15 minutes to obtain a coating agent. Comparative Example 5 was different from Example 1 in that BT was added in an unswollen state. From the coating agent obtained, a film was obtained by the method of Example 1, and water vapor permeability was measured.

Comparative Example 6

To 653.1 parts by mass of water were added 22.6 parts by mass of Eudragit® RL30D (30% water dispersions) (Rohm), 6.8 parts by mass of PVA, and 212.5 parts by mass of BT solution, and the resulting mixture was stirred with a homogenizer to obtain a coating agent. A coated solid preparation was obtained by the method of Example 1, and the appearance change of tablets over time was observed. A film was also obtained by the method of Example 1, and water vapor permeability was measured.

Comparative Example 7

To 736.5 parts by mass of water were added 5.0 parts by mass of microcrystalline cellulose, 5.0 parts by mass of ethyl cellulose, 2.5 parts by mass of PVA, 125.0 parts by mass of BT solution, and 1.0 parts by mass of glycerin fatty acid ester, and the resulting mixture was stirred with a homogenizer to obtain a coating agent. A coated solid preparation was obtained by the method of Example 1, and the appearance change of tablets over time was observed. A film was also obtained by the method of Example 1, and water vapor permeability was measured.

Comparative Example 8

To 225.0 parts by mass of water were added 15.0 parts by mass of PVA and 10.0 parts by mass of talc, and the resulting mixture was stirred with a homogenizer to obtain a coating agent. Talc is a nonswelling clay mineral. A coated solid preparation was obtained by the method of Example 1, and the appearance change of tablets over time was observed. A film was also obtained by the method of Example 1, and water vapor permeability was measured.

Table 2 shows the deliquescence (appearance change) of the tablets and the water vapor permeability of the films, which tablets and films were obtained in Example 6 and Comparative Examples 5 to 8. In the table, the symbol "o" means no change, and "x" means that the exudation of deliquesced drugs out of the tablets was observed.

TABLE 2

| | Composition | Deliquescence 2-week storage | Water vapor permeability of film (g · mm/cm$^2$ · 24 hr · atm) |
|---|---|---|---|
| Example 6 | PVA/BT/Span 20 = 26.4/61.6/12 | o | $1.9 \times 10^{-5}$ |
| Comparative Example 5 | PVA/BT = 8/2 | — | $2.7 \times 10^{-4}$ |
| Comparative Example 6 | PVA/BT/Eudragit RL30D = 1/1/1 | x | $2.6 \times 10^{-4}$ |
| Comparative Example 7 | PVA/BT/Microcrystalline cellulose/EC/Glycerin fatty acid ester = 14.3/22.8/28.6/28.6/5.7 | x | $3.6 \times 10^{-4}$ |
| Comparative Example 8 | PVA/Talc = 6/4 | x | $4.8 \times 10^{-4}$ |

The results of Example 6 shows that, in the case where nonionic surfactants were added to PVA/BT, water vapor permeability of the film was not more than $1.0 \times 10^{-4}$ and deliquescence was not observed even after 2-week storage. The comparison of Example 2 and Comparative Example 5 showed that it is preferred that BT should be added in a swollen state rather than as powders. In the tablets of Comparative Example 6 and Comparative Example 7 which were coated with a moisture-proof coating composition (coating agent) composed of water-insoluble materials, the water vapor permeability of the films were greater than $1.0 \times 10^{-4}$ and deliquescence was observed after 2-week storage, from which it was proved that the moisture-proof coating composition using the prior art was not able to provide sufficient stability against moisture. Further, the comparison of Comparative Example 8 and Example 5 showed that blending swelling clay significantly improved moisture barrier properties.

Example 7

For the coated tablets obtained in Example 6 and the tablets which were obtained by leaving the tablets to stand under the conditions of 25° C. and 60% RH, dissolution tests were performed. The dissolution tests were in accordance with the Japanese Pharmacopoeia, 15th Edition, Dissolution Test, Second Method; the tablets were placed into 900 mL of distilled water and the drug release rate at 8, 11, and 20 hours after the start of the dissolution was quantitatively determined by HPLC.

(HPLC Conditions)

Mobile phase: 50 mM sodium dihydrogen phosphate/acetonitrile=5/5 (v/v)

Column: Devolosil ODS-5 (4.6×150 mm)

Detection wavelength: 210 nm

Comparative Example 9

For sodium valproate sustained-release tablets (Selenica R 200 mg; Kowa Company, Ltd.) and the tablets left to stand under the conditions of 25° C. and 60% RH, dissolution test was performed by the method of Example 7.

Table 3 shows the results of the dissolution tests of Example 7 and Comparative Example 9.

TABLE 3

| | Storage period | Release rate (%) | | |
| --- | --- | --- | --- | --- |
| | | 8 hours | 11 hours | 20 hours |
| Example 7 | Initial | 17 | 38 | 81 |
| | 2 weeks | 14 | 32 | 79 |
| | 4 weeks | 16 | 34 | 81 |
| Comparative Example 9 | Initial | 16 | 39 | 84 |
| | 1 day | 77 | 82 | 90 |

These results confirmed that the tablets in Example 7 exhibited the equivalent release rate to that of Selenica R 200 mg tablets (see Initial of Comparative Example 9), commercially available sustained-release tablets, until after 4-week storage. In Comparative Example 9, on the other hand, the release rate significantly increased only after 1-day storage from the value of Selenica R 200 mg tablets (see Initial of Comparative Example 9) because of the deliquescence of drugs. Thus, the solid preparation proved to have good release properties as well as stability against moisture.

Example 8

To the coating pan (DRC-200; Powrex), 200 g of sodium valproate conventional tablets (Depakene 200 mg; Kyowa Hakko) were loaded, and the tablets were coated with the coating agent prepared in Example 1 to a coating thickness of 20 µm. For the coated solid preparation obtained, the appearance change of the tablets over time when left to stand under the conditions of 25° C. and 60% RH was observed.

Example 9

To the coating pan (DRC-200; Powrex), 200 g of sodium valproate conventional tablets (Depakene 200 mg; Kyowa Hakko) were loaded, and the tablets were coated with the coating agent prepared in Example 6 to a coating thickness of 20 µm. For the coated solid preparation obtained, the appearance change of the tablets over time when left to stand under the conditions of 25° C. and 60% RH was observed.

Comparative Example 10

The appearance change of the tablets over time when sodium valproate conventional tablets (Depakene 200 mg; Kyowa Hakko) were left to stand under the conditions of 25° C. and 60% RH was observed.

Table 4 shows the appearance change over time of the tablets obtained in Example 8, Example 9, and Comparative Example 10. In the table, the symbol "o" means no change, and "x" means that the exudation of deliquesced drugs out of the tablets was observed.

TABLE 4

| | PVA/BT/Span 20 | Deliquescence | |
| --- | --- | --- | --- |
| | | 2-week storage | 4-week storage |
| Example 8 | 5/5/0 | o | o |
| Example 9 | 26.4/61.6/12 | o | o |
| Comparative Example 10 | — | x | x |

Table 4 shows that the solid preparation is applicable to immediate-release tablets as well as sustained-release tablets because it can sufficiently suppress deliquescence even when the inner layers are conventional tablets (immediate-release tablets).

INDUSTRIAL APPLICABILITY

The solid preparation is useful as a solid preparation that can be packed in a one-dose pack because the valproic acid or a pharmacologically acceptable salt thereof contained therein is excellent in long-term stability against moisture and it has good release properties. The solid preparation that can be packed in a one-dose pack has the great industrial merit in that it improves drug compliance of patients, which in turn leads to improved therapeutic effects.

The invention claimed is:

1. A coated solid preparation comprising:
    a solid preparation comprising valproic acid or a pharmacologically acceptable salt thereof as an active ingredient; and
    a coating layer containing polyvinyl alcohol and a swelling clay chosen from a smectite coating the solid preparation; wherein a mass ratio of the polyvinyl alcohol to the swelling clay is 8:2 to 3:7; and wherein
    the swelling clay in the coating layer is homogenously dispersed as a laminated structure and bands of the swelling clay have consecutive and continuous contacting surfaces with each other.
2. The coated solid preparation according to claim 1, wherein the swelling clay chosen from a smectite is bentonite or magnesium aluminum silicate.
3. The coated solid preparation according to claim 1, wherein water vapor permeability of the coating layer is $1.0 \times 10^{-5}$ to $1.0 \times 10^{-4}$ g·mm/cm$^2$·24 hr·atm.
4. The coated solid preparation according to claim 2, wherein water vapor permeability of the coating layer is $1.0 \times 10^{-5}$ to $1.0 \times 10^{-4}$ g·mm/cm$^2$·24 hr·atm.

* * * * *